United States Patent
Johansen et al.

(10) Patent No.: US 7,303,533 B2
(45) Date of Patent: Dec. 4, 2007

(54) SHAPEABLE INTRALUMINAL DEVICE AND METHOD THEREFOR

(75) Inventors: Jerald A. Johansen, Canyon Lake, CA (US); Diego D. Cueto, Dana Point, CA (US)

(73) Assignee: Intraluminal Therapeutics, Inc., Carlsbad, CA (US)

( * ) Notice: Subject to any disclaimer, the term of this patent is extended or adjusted under 35 U.S.C. 154(b) by 26 days.

(21) Appl. No.: 10/249,453

(22) Filed: Apr. 10, 2003

(65) Prior Publication Data

US 2005/0261607 A1 Nov. 24, 2005

(51) Int. Cl.
*A61B 5/00* (2006.01)
*A61M 25/00* (2006.01)

(52) U.S. Cl. ..................................... 600/585

(58) Field of Classification Search ............. 600/433, 600/434, 435, 585; 604/164.01, 164.13, 604/170.01, 171
See application file for complete search history.

(56) References Cited

U.S. PATENT DOCUMENTS

| | | | |
|---|---|---|---|
| 3,773,034 A | 11/1973 | Burns et al. | |
| 4,906,230 A | 3/1990 | Maloney et al. | |
| 4,909,787 A | 3/1990 | Danforth | |
| 4,964,409 A | 10/1990 | Tremulis | |
| 5,061,273 A | 10/1991 | Yock | |
| 5,167,239 A | 12/1992 | Cohen et al. | |
| 5,201,754 A * | 4/1993 | Crittenden et al. | 606/194 |
| 5,344,402 A | 9/1994 | Crocker | |
| 5,410,797 A * | 5/1995 | Steinke et al. | 29/435 |
| 5,498,239 A | 3/1996 | Galel et al. | |
| 5,505,699 A | 4/1996 | Forman et al. | |
| 5,569,197 A | 10/1996 | Helmus et al. | |
| 5,619,993 A | 4/1997 | Lee | |
| 5,664,580 A * | 9/1997 | Erickson et al. | 600/585 |
| 5,741,429 A * | 4/1998 | Donadio et al. | 216/8 |
| 5,807,249 A | 9/1998 | Qin et al. | |
| 5,833,632 A | 11/1998 | Jacobsen et al. | |
| 5,951,482 A | 9/1999 | Winston et al. | |
| 5,997,487 A | 12/1999 | Kolehmainen et al. | |
| 6,013,072 A | 1/2000 | Winston et al. | |
| 6,027,462 A | 2/2000 | Greene et al. | |
| 6,048,349 A | 4/2000 | Winston et al. | |
| 6,059,739 A | 5/2000 | Baumann | |
| 6,063,093 A | 5/2000 | Winston et al. | |
| 6,123,698 A | 9/2000 | Spears et al. | |
| 6,146,338 A | 11/2000 | Gardeski et al. | |
| 6,165,123 A | 12/2000 | Thompson | |
| 6,217,527 B1 | 4/2001 | Selmon et al. | |
| 6,221,049 B1 | 4/2001 | Selmon et al. | |
| 6,231,546 B1 | 5/2001 | Milo et al. | |
| 6,235,000 B1 | 5/2001 | Milo et al. | |
| 6,235,007 B1 | 5/2001 | Divino, Jr. et al. | |
| 6,375,628 B1 | 4/2002 | Zadno-Azizi et al. | |
| 6,394,976 B1 | 5/2002 | Winston et al. | |
| 6,406,442 B1 | 6/2002 | McFann et al. | |
| 6,463,313 B1 | 10/2002 | Winston et al. | |
| 2001/0000041 A1 | 3/2001 | Selmon et al. | |

(Continued)

*Primary Examiner*—Max F. Hindenburg
*Assistant Examiner*—Jonathan Foreman
(74) *Attorney, Agent, or Firm*—Armstrong Teasdale, LLP

(57) ABSTRACT

A hollow medical device includes a coil member having a distal end, a proximal end, a plurality of turns extending therebetween, and a lumen extending through the turns. The coil member further includes at least one weld extending from one turn to an adjacent turn.

31 Claims, 3 Drawing Sheets

U.S. PATENT DOCUMENTS

2001/0012924 A1    8/2001   Milo et al.
2002/0032391 A1    3/2002   McFann et al.
2003/0013985 A1    1/2003   Saadat
2003/0088210 A1*   5/2003   Miskolczi et al. ....... 604/99.02
2003/0130712 A1*   7/2003   Smits et al. ................ 607/116

* cited by examiner

SHAPEABLE INTRALUMINAL DEVICE AND METHOD THEREFOR

BACKGROUND OF INVENTION

This invention relates generally to intraluminal devices used in medical interventional procedures, and in particular to vascular interventions.

Intraluminal devices, e.g., guide wires, are steered through body passages such as arteries or veins by shaping the wire and then manipulating the proximal end of the wire while pushing the wire through the passage. Often, the wires are manipulated under x-ray visualization. By rotating the proximal end of the wire, the shape formed in the distal end changes orientation allowing the operator to select directions, especially where the vessel divides into multiple paths.

Being able to shape the guide wire, especially its distal end, is important to the effectiveness of the particular guide wire as an intervention tool. Operators have a strong preference to form their own shape in the wire, often customizing the wire to the specific anatomy through which the guide wire is being navigated.

Guide wires are described extensively in the art. Most of the guide wires are designed around a central core element with a wire or ribbon of material wrapped around the central core. The core imparts many of the mechanical properties of the wire and is generally responsible for allowing the guide wire to be shaped. These guide wires are typically shaped by imparting plastic deformation to the core which retains this deformation during use of the guide wire.

For most interventional procedures the guide wire acts as a rail to allow other devices, such as angioplasty balloons and stents, to be placed precisely in a vessel. However, guide wires themselves have evolved to be therapeutic devices. For example, balloons or wire meshes have been placed within the guide wire structure to become distal embolic protection devices during interventions. Guide wires also have been used to conduct radio frequency energy to ablate tissue.

Often, the central core of the guide wire has to be removed or eliminated to allow other functional elements to be added to the wire while minimizing the profile of the guide wire so it can be advanced into smaller body vessels. Such guide wires include, but are not limited to, infusion guide wires capable of delivering drugs or therapeutic materials such as embolic agents; guide wires with removable central cores; hollow core wires for pressure measurements; and guide wires that have optical fibers to visualize or deliver light energy.

SUMMARY OF INVENTION

In accordance with one aspect of the invention, a hollow medical device is provided that comprises a coil member. The coil member comprises a distal end, a proximal end, a plurality of turns extending therebetween, and a lumen extending through said turns. The coil member further comprising at least one weld extending from one turn to an adjacent turn.

In another aspect of the invention, a method is provided for shaping an intraluminal device having a coiled member. The method comprising forming the coil member including a distal end, a proximal end, a plurality of turns extending between the proximal end and the distal end, and a lumen extending through the turns, connecting at least one turn of the coil member to an adjacent turn, and bending the coil member at the connected turns into a shape suitable to traverse a body lumen.

In a further aspect of the invention, a medical device is provided for insertion into a body lumen. The medical device comprising a coil comprising a plurality of turns, a lumen extending through the turns, and at least one weld extending from a first turn to an adjacent turn.

DETAILED DESCRIPTION

Figure 1:
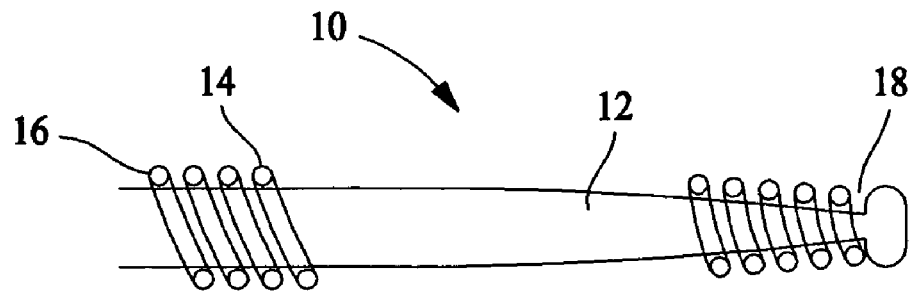
FIG. 1 illustrates a portion of a conventional guide wire that includes a central core element and a wire wound coil that forms the outer portion of the guide wire.

Exemplary embodiments of shapeable intraluminal devices and methods of providing and using shapeable intraluminal devices are described below. In one embodiment, the shapeable device is a guide wire having a shapeable tip formed from a coil with adjacent turns fastened together and a lumen extending through the turns of the coil. The shapeable tip maintains its shape due, at least in part, to the attachment of adjacent coils. The lumen allows passage of fluids, e.g., drugs or reagents, therethrough. In an alternative embodiment, the shapeable tip includes components such as optic fibers, tubes, balloons, and wire meshes. The shapeable tip can be shaped to allow the operator to steer the wire by conventional rotating techniques from outside the patient's body.

Although exemplary embodiments are described herein, the intraluminal devices and methods are not limited to those specific embodiments. For example, although an exemplary embodiment of a guide wire is described below in detail, it is to be understood that the shapeable coil of the present invention is applicable to catheters as well as other medical device utilizing a coil that is to retain a bent or curved configuration. As another example, although the present invention is described in the context of a shapeable tip, it is to be understood that the shapeable coil, or portion of the coil, can be positioned at any location along the length of the medical device. As a further example, although the method of attaching adjacent turns of the coil is described as welding, it is to be understood that attachment methods such as brazing and soldering are also applicable to the present invention.

The intraluminal devices and methods are illustrated with reference to the figures wherein similar numbers indicate the same elements in all figures. Such figures are intended to be illustrative rather than limiting and are included herewith to facilitate explanation of an exemplary embodiment of the devices and methods of the invention.

Guide wires are generally constructed from many materials. Specifically, the central core and coils of known guide wires are typically manufactured from metallic and non-metallic wires or ribbons, e.g., stainless steel, Nitinol, and polymers. Stainless steels are utilized due to their ductility, corrosion resistance, and ability to be easily sterilized. Nitinol, a nickel-titanium alloy, is useful for its unique superelastic and shape memory properties. In addition, coils can also be fabricated from heavy metals such as platinum, platinum-iridium, and gold for radiopacity. Graphite non-metallic fibers have also been used in composite materials. Coils are commercially available from many sources or can be custom wound. Such coils can be wound from single strands or can be cable-like with multiple filars. One important aspect of guide wires, as well as other intraluminal medical devices, is that they have a low profile. For guide wires, profiles less than 0.038 inches outer diameter are typically desirable and profiles as low as 0.010 inches outer diameter are sometimes desirable.

FIG. 1 illustrates a portion of a conventional guide wire 10 that includes a central core element 12 and a wire wound coil 14 that forms the outer portion of guide wire 10. Central core element 12 helps to transmit torque from a first end 16 of the wire to a second end 18 and is responsible for many of the mechanical properties of guide wire 10 such as stiffness and rigidity. Central core element 12 also allows a shape to be imparted to, and retained by, wire 10 by bending core element 12 plastically so that an angle or curve is retained in guide wire 10. Wound coil 14 provides flexibility to guide wire 10 for navigating tortuous paths while being able to transmit rotational movement in a smooth transition from first end 16 to second end 18.

Figure 2:
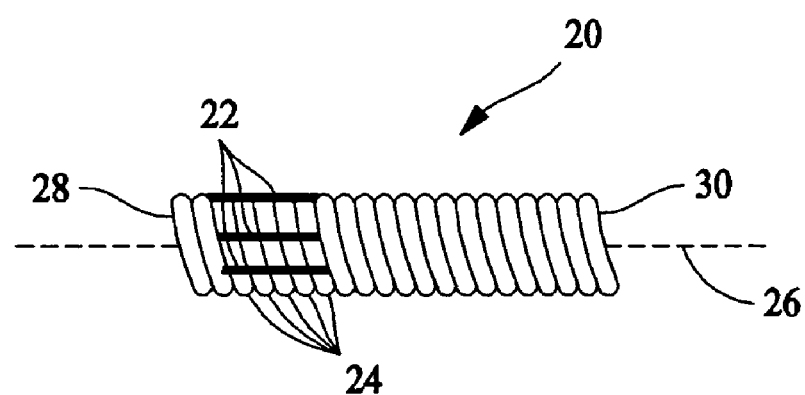
FIG. 2 illustrates a shapeable coil in accordance with one embodiment of the invention.

FIG. 2 illustrates a shapeable coil 20 in accordance with one embodiment of the invention. Coil 20 includes a lumen (not shown) extending through an interior of coil 20 and a plurality of welds 22 connecting adjacent turns 24 of coil 20. Since coil 20 does not include a central core, a shape retention member is incorporated into coil 20. Coil 20 is fabricated to perform as a shape retention member by the joining of adjacent turns 24. This joining of adjacent turns 24 creates a structural member that is stiffer than a coil without joined adjacent turns and that can be plastically deformed. For metal coils, this fabrication is performed by precision welding techniques including laser, electron beam, pulse-arc, and parallel gap resistance welding. In an alternative embodiment, the joining of adjacent turns 24 of coil 20 utilizes brazing or soldering techniques. As a further alternative, for metallic and non-metallic coils, this fabrication utilizes applications of adhesives including glues, epoxies, and metal-filled epoxies.

Welding adjacent turns 24 of coil 20 allows a ductile member to be formed from a portion of coil 20. The heat-affected zone around welds 22 essentially anneals turns 24 allowing them to remain flexible. Welded coil 20 is plastically deformable by an operator to a desired shape and although there may be some recoil (elastic deformation) of the deformed coil, this recoil can be corrected by over shaping the component to compensate for the recoil.

The degree of stiffness of coil 20 and a guide wire into which coil 20 is located can be controlled by the depth and/or thickness of weld 22 as well as the number of welds 22. In one embodiment, the weld extends between two adjacent turns. In an alternative embodiment, the weld extends between at least three adjacent turns. In an exemplary embodiment, weld 22 is parallel to an axis 26 of coil 20 that extends from a first end 28 of coil 20 to a second end 30 of coil 20. In alternative embodiments, welds 22 are formed in parallel to each other and/or in intersecting patterns in the area that is intended to be shaped or made stiffer. In addition, welds 22 can be continuous or spot welds.

Figure 3:
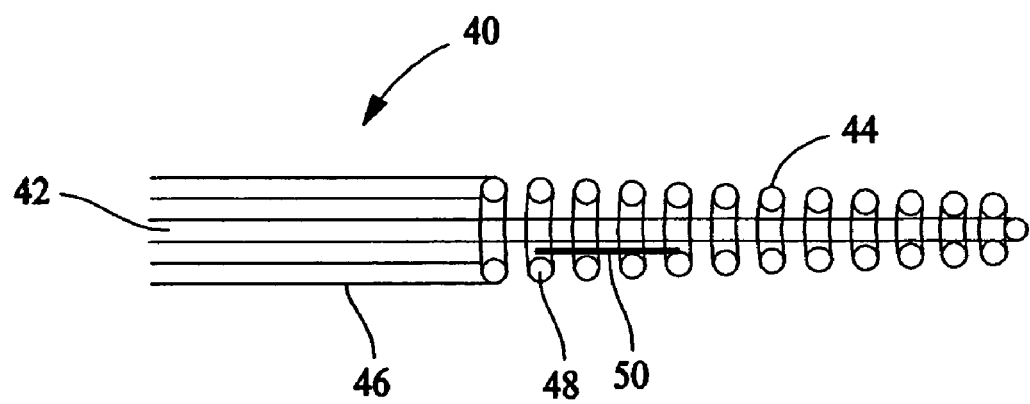
FIG. 3 illustrates a portion of a guide wire including an optical fiber member surrounded by a wire wound coil.

FIG. 3 illustrates a portion of a guide wire 40 including an optical fiber member 42 surrounded by a wire wound coil 44. In one embodiment, optical fiber member 42 is a single optical fiber. In an alternative embodiment, optical fiber member 42 is a bundle of optical fibers. Guide wire 40 also includes a tube 46 connected to a proximal end of coil 44. Coil 44 includes a plurality of turns 48 and a weld 50 connecting adjacent turns.

Figure 4:
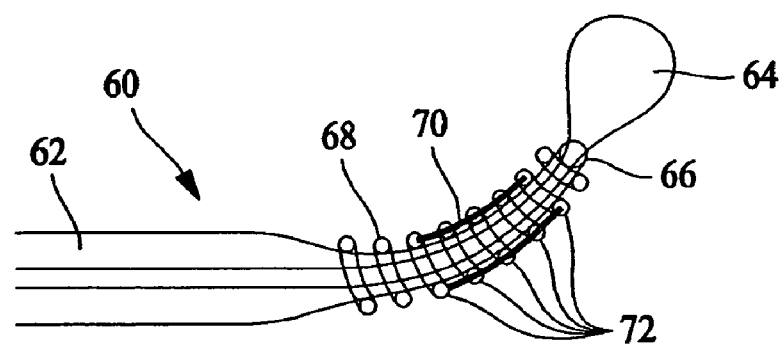
FIG. 4 illustrates a portion of a guide wire including a tube utilized to inflate a balloon at a distal end of the guide wire.

FIG. 4 illustrates a portion of a guide wire 60 including a tube 62 utilized to inflate a balloon 64 at a distal end 66 of guide wire 60. Guide wire 60 also includes a coil 68 including a pair of welds 70 joining adjacent turns 72. Coil 68 is illustrated in a bent configuration. As illustrated, the bent shape imparted to coil 68 is maintained by plastic deformation of welds 70. Guide wire 60 is utilized, in one embodiment, for occluding a vessel to trap material during a therapy, e.g., block an artery to protect against distal embolization during an angioplasty.

Figure 5:
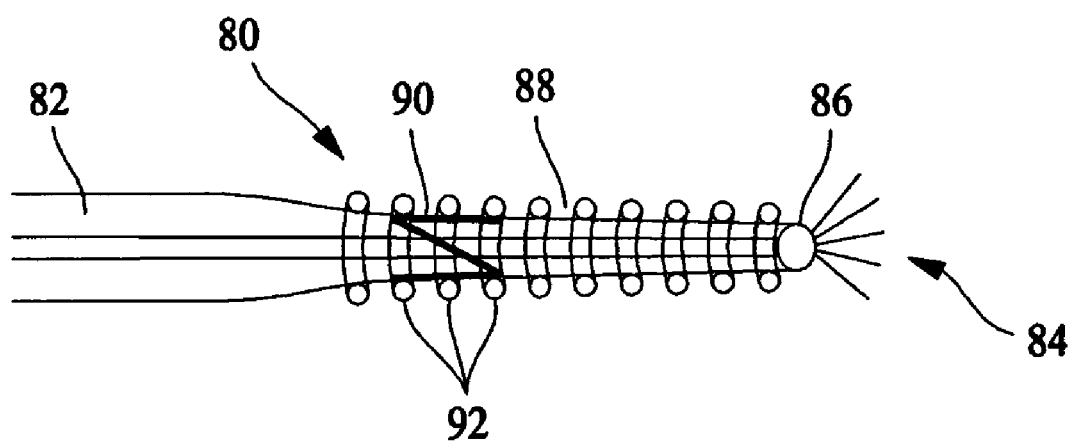
FIG. 5 illustrates a guide wire including a tube utilized to deliver drugs or reagents to a distal tip of, or to some intermediate point along the length of, the guide wire.

FIG. 5 illustrates a guide wire 80 including a tube 82 utilized to deliver drugs or reagents 84 to a distal tip 86 of, or to an intermediate point along the length of, guide wire 80. Guide wire 80 also includes a coil 88 including a plurality of welds 90 formed in a pattern that connect adjacent turns 92. Guide wire 80, in one embodiment, is a perfusion device.

A method of forming coils 20, 44, 68, and 88 includes manufacturing a straight wire or ribbon. The wire or ribbon is then wound around a mandrel to form a coil. Welds, such as welds 22, 50, 70, and 90 are applied to the coil in the areas likely to require shaping to accomplish the intended use of the device. In one embodiment, the welds are located at the distal end of the coil. In alternative embodiments, the welds are located at other positions along the coil. The interventional operator then forms a shape into the wire in the area of the welds. In one embodiment, the shaping is imparted by pinching the coil between the operator's fingers. Alternatively, the shaping is imparted by rolling the coil across the sides of curved instrument, e.g., forceps or a rod. In a further alternative embodiment, the coil is shaped according to other methods. Although the coil is typically shaped prior to entry of the coil into a body, the coil can be shaped by a user at any time during a procedure simply by removing the device from the body and reshaping the coil to accommodate the anatomy.

While the invention has been described in terms of various specific embodiments, those skilled in the art will recognize that the invention can be practiced with modification within the spirit and scope of the claims.

The invention claimed is:

1. A hollow medical device comprising a coil member comprising a distal end, a proximal end, a plurality of turns extending therebetween, and a lumen extending through said turns, said coil member comprising a plurality of intersecting welds extending from one turn to an adjacent turn to provide stiffness to said coil, and plurality of non-intersecting welds extending from one turn to an adjacent turn to form at least one ductile member, said coil member configured to be plastically deformed by bending said ductile member at the plurality of non-intersecting welds, such that said ductile member retains a bent shape of said coil member.

2. A hollow medical device in accordance with claim 1 wherein said device comprises one of a catheter and a guide wire.

3. A hollow medical device in accordance with claim 1 further comprising a tube within said lumen.

4. A hollow medical device in accordance with claim 1 wherein said coil member comprises at least one of a helical coil of wire and a wound ribbon.

5. A hollow medical device in accordance with claim 1 wherein said coil member includes an axis extending from said proximal end to said distal end, said plurality of non-intersecting welds substantially parallel to said axis.

6. A hollow medical device in accordance with claim 1 wherein at least one of said plurality of non-intersecting welds connects at least three adjacent turns.

7. A hollow medical device in accordance with claim 1 wherein said device further comprises a distal tip, said distal end connected to said distal tip.

8. A hollow medical device in accordance with claim 1 further comprising a tubular member extending from said proximal end of said coil member to a handle.

9. A hollow medical device in accordance with claim 1 wherein said coil member lumen is devoid of internal members.

10. A hollow medical device in accordance with claim 1 wherein a portion of said turns are annealed and flexible.

11. A hollow medical device in accordance with claim 1 wherein said coil member comprises metal.

12. A hollow medical device in accordance with claim 11 wherein said metal is at least one of steel and nitinol.

13. A method for shaping an intraluminal device having a coiled member, said method comprising:
    forming the coil member including a distal end, a proximal end, a plurality of turns extending between the proximal end and the distal end, and a lumen extending through the turns;
    welding a plurality of intersecting welds that extend from one turn to an adjacent turn to provide stiffness to said coil;
    welding a plurality of non-intersecting welds that extend from one turn to an adjacent turn to form a ductile member; and
    plastically bending the ductile member at the plurality of non-intersecting welds into a bent shape suitable to traverse a body lumen, such that the ductile member retains the bent shape of the coil member.

14. A method in accordance with claim 13 wherein plastically bending the coil member comprises plastically deforming the coil member at the plurality of non-intersecting welds.

15. A method in accordance with claim 13 wherein welding comprises at least one of welding and soldering the at least one turn of the coil member to an adjacent turn.

16. A method in accordance with claim 13 wherein connecting further comprising welding at least three adjacent turns.

17. A method in accordance with claim 13 wherein the coil member lumen is devoid of internal members, bending the coil member at the connected turns into a shape suitable to traverse a body lumen comprises bending the lumen devoid of internal members at the connected turns into a shape suitable to traverse a body lumen.

18. A method in accordance with claim 13 further comprising connecting the proximal end of the coiled member to a tubular member.

19. A method in accordance with claim 13 further comprising extending a tubular member through the coil member lumen.

20. A method in accordance with claim 13 further comprising extending a balloon member through the coil member lumen.

21. A method in accordance with claim 13 further comprising extending at least one fiber optic member through the coil member lumen.

22. A medical device for insertion into a body lumen, said medical device comprising a coil comprising a plurality of turns, a plurality of intersecting welds that extend from one turn to an adjacent turn to provide stiffness to said coil, a plurality of non-intersecting welds that extend from one turn to an adjacent turn to form a ductile member, and a lumen extending through said turns, said coil configured to be plastically deformed by bending said coil at said ductile member, such that said ductile member retains a bent shape of said coil member.

23. A medical device in accordance with claim 22 wherein said coil member lumen is devoid of internal members.

24. A medical device in accordance with claim 22 wherein said device comprises one of a catheter and a guide wire.

25. A medical device in accordance with claim 22 further comprising a tube within said lumen.

26. A medical device in accordance with claim 22 wherein said coil comprises at least one of a helical coil of wire and a wound ribbon.

27. A medical device in accordance with claim 22 wherein said coil comprises is at least one of steel and nitinol.

28. A medical device in accordance with claim 22 wherein said plurality of non-intersecting welds are substantially parallel to said turns.

29. A medical device in accordance with claim 22 wherein at least one of said plurality of non-intersecting welds connects at least three adjacent turns.

30. A medical device in accordance with claim 22 further comprising a tubular member extending from said coil to a handle.

31. A medical device in accordance with claim 22 wherein a portion of said turns are annealed and flexible.

* * * * *